United States Patent [19]
Leadbitter

[11] Patent Number: 5,843,982
[45] Date of Patent: Dec. 1, 1998

[54] FUNGICIDAL COMPOSITIONS COMPRISING METALAXYL AND FLUDIOXONIL

[75] Inventor: Neil Leadbitter, Therwil, Switzerland

[73] Assignee: Novartis Finance Corporation, New York, N.Y.

[21] Appl. No.: 799,310

[22] Filed: Feb. 14, 1997

[30] Foreign Application Priority Data

Feb. 15, 1996 [CH] Switzerland ............................. 395/96

[51] Int. Cl.$^6$ .......................... A01N 37/12; A01N 37/44; A01N 43/36
[52] U.S. Cl. ............................. 514/422; 514/538
[58] Field of Search ...................... 514/422, 538

[56] References Cited

U.S. PATENT DOCUMENTS 4,151,299   4/1979   Hubele ..................... 424/309
4,780,551   10/1988  Nyfeler et al. ............. 549/422

FOREIGN PATENT DOCUMENTS

96/01559   1/1996   WIPO .
9601559    1/1996   WIPO .
9601560    1/1996   WIPO .

OTHER PUBLICATIONS

C.Tomlin (ED.): "The Presticide Manual", British Corp Protection Council, 10. Auflage, 1994, Siehe Zeite 482: Fludioxonyl, Mixtures.

Recent Progress in the Field of N–Acylalanines as Systemic Fungicides, Gozzo, Boschi, Garlaschelli, Zagni, Overeem & Vries, vol. 16, no. 3, pp. 277–286 (1985).

Systemische Fungizide Und Antifungale Verbindungen, Abhandlungen der Akademie der Wissenschaften der DDR, vol. 1982, p. 123–133 (1983).

Tomlin, "The Pesticide Manual Incorporating the Agrochemicals Handbook", 10th Ed. (1995) pp. 482–483.

*Primary Examiner*—Allen J. Robinson
*Attorney, Agent, or Firm*—Michael P. Morris

[57] ABSTRACT

When used in admixture with fludioxonil, metalaxyl having a high R-enantiomer content of more than 70% by weight, or pure R-metalaxyl, exhibits a markedly enhanced fungicidal action against plant diseases. At the same time, the high R-enantiomer content accelerates the degradability of metalaxyl in the soil.

12 Claims, No Drawings

FUNGICIDAL COMPOSITIONS COMPRISING METALAXYL AND FLUDIOXONIL

The present invention relates to fungicidal two-component mixtures based on metalaxyl which has an R-enantiomer content of more than 70% by weight, and to their use for controlling and preventing infestation by Oomycetes. The R-metalaxyl component is called active ingredient I.

More specifically, the invention relates to mixtures based on metalaxyl having an R-enantiomer content of more than 85% by weight, preferably of more than 92% by weight and, particularly preferably, containing pure R-enantiomer (I) which is substantially free of S-enantiomer.

Metalaxyl of formula

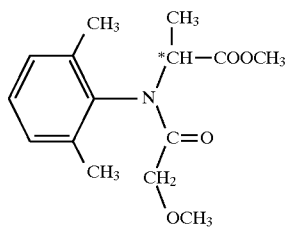

has an asymmetric *C-atom and can be resolved into the enantiomers in customary manner (GB-P.1,500,581). Since 1975 it has been known to those skilled in the art that the R-enantiomer is far superior to the S-enantiomers in terms of fungicidal action and is in practice regarded as the actual mechanism of action. Commercial metalaxyl is available in the form of the racemate. Likewise, mixtures of metalaxyl racemate with mancozeb, chlorothalonile, copper preparations, folpet, fluazinam or cymoxanil have become known commercially and otherwise. Owing to its high activity, there has in the past never been any practical necessity to resolve the racemate, of which half consists of the desired R-enantiomer. Today, metalaxyl is a standard formulation for controlling downy mildew varieties (Oomycetes).

As soon as metalaxyl has a high R-enantiomer content, the degradability of the formulation in the soil rapidly increases as compared to racemic metalaxyl (WO-96/01559). For ecological reasons, a formulation which is enriched with R-metalaxyl is therefore particularly suitable as mixing component for applications above the soil to crops of cultivated plants, but especially for seed dressing and, preferably, for soil applications where long residence times of a pesticide are undesirable.

It has now been found, completely surprisingly, that R-metalaxyl in pure or in more than 70% form, in admixture with the fungicide fludioxonil [=4-(2,2-di-fluoro-1,3-benzodioxol-7-yl)-1H-pyrrol-3-carbonitrile of formula II

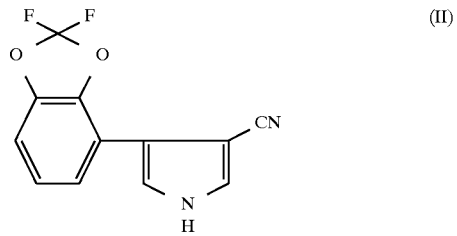

(EP-A-206 999) achieves markedly enhanced actions against plant pathogens and is suitable for foliar application in living crops of plants as well as, in particular, for dressing applications on plant propagation material. The latter term embraces seeds of all kinds (fruit, tubers, grains), cuttings, cut shoots and the like. The preferred field of application is the treatment of all kinds of seeds, in particular the seed treatment of cereal.

In addition to the two-component mixture I+II, this invention also relates to a method of controlling fungi, which comprises treating a site, for example a plant, that is infested or liable to be infested by fungi with a) the active ingredient I and with b) the active ingredient of formula II in any desired sequence or simultaneously.

Advantageous mixing ratios of the two active ingredients are I:II=from 10:1 to 1:30, preferably I:II=from 7:1 to 1:20. In many cases, mixtures in which the mixing ratio of the active substances I:II is from 7:1 to 1:10, e.g. from 7:1 to 1:1 are advantageous. Other advantageous mixing ratios are 6:1, 7:2, 2:3.

The novel active ingredient mixtures I+II have very advantageous curative, preventive and systemic fungicidal properties for protecting cultivated plants. As has been mentioned, said active ingredient mixtures can be used to inhibit or destroy the microorganisms that occur on plants or parts of plants (fruit, blossoms, leaves, stems, tubers, roots) of different crops of useful plants, while at the same time those parts of plants which grow later are also protected from attack by such microorganisms. This applies, in particular, also to those microorganisms which have developed reduced sensitivity against metalaxyl. Active ingredient mixtures I+II have the special advantage of being highly active against diseases in the soil which mostly occur in the early stages of plant development. Pathogens are mainly Pythium, Tilletia, Gerlachia, Septoria, Ustilago, Fusarium, Rhizoctonia (so-called "damping off complex"). The novel mixture is also active against Oomycetes such as Phytophthora, Plasmopara, Pseudoperonospora, Bremia etc. as well as against the Botrytis species, Pyrenophora, Monilinia and further representatives of the Ascomycetes, Deuteromycetes and Basidiomycetes classes.

In a particular embodiment of this invention, difenoconazol can be added as further active ingredient III to the two-component mixture in the dressing application. Difenoconazol is 1-{2-[2-chloro-4(4-chlorophenoxy)phenyl]-4-methyl-1,3-dioxolan-2-ylmethyl}-1H-1,2,4-triazole and is described in GB-2 098 607.

Three-component mixtures for dressing are preferably those having mixing ratios I:II:III of about 6:1:10, for example 15 g:2.5 g:24 g a.i./100 kg or 37.5 g:6.25 g:60 g a.i./100 kg of seeds.

The active ingredient mixtures of formulae I and II are normally used in the form of formulations. R-Metalaxyl (formula I) and the active ingredient of formula II can be applied to the area or plant to be treated simultaneously or in immediate succession, if desired together with further carriers, surfactants or other application-promoting adjuvants customarily employed in formulation technology.

Suitable carriers and adjuvants can be solid or liquid and are the substances customarily employed in formulation technology, for example natural or regenerated mineral substances, solvents, dispersants, wetting agents, tackifiers, thickeners, binders or fertilisers.

The compounds of this combination are used in unmodified form or, preferably, together with the adjuvants conventionally employed in formulation technology. To this end they are conveniently formulated in known manner e.g. to emulsifiable concentrates, coatable pastes, directly sprayable or dilutable solutions, dilute emulsions, wettable powders, soluble powders, dusts, granulates, and also by encapsulation in e.g. polymer substances. As with the nature of the compositions, the methods of application, such as spraying, atomising, dusting, scattering, coating or pouring, are chosen in accordance with the intended objectives and the prevailing circumstances. Advantageous rates of application of the active ingredient mixture are normally from 0.5 g to 400 g a.i./ha, preferably form 1 g to 250 g a.i./ha.

The formulations are prepared in known manner, typically by intimately mixing and/or grinding the active ingredients with extenders, e.g. solvents, solid carriers and, where appropriate, surface-active compounds (surfactants).

The agrochemical compositions usually comprise 0.1 to 99%, preferably 0.1 to 95%, of active ingredients of formulae I and II, 99.9 to 1%, preferably 99.9 to 5%, of a solid or liquid adjuvant, and 0 to 25%, preferably 0.1 to 25%, of a surfactant.

Whereas commercial products or wet or dry dressings will preferably be formulated as concentrates, the end user will normally use dilute formulations for developing plants.

Suitable target crops are especially potatoes, cereals, (wheat, barley, rye, oats, rice), maize, sugar beet, cotton, millet varieties such as sorghum, sun flowers, beans, peas, oil plants such as rape, soybeans, cabbages, tomatoes, eggplants (aubergines), pepper and other vegetables and spices as well as ornamental shrubs and flowers.

A preferred method of applying a mixture of active ingredients of formulae I and II or an (agro)chemical composition comprising these active ingredients (with the optional addition of difenoconazol as active ingredient III), is foliar application. The frequency of application and the rate of application will depend on the risk of infestation by the corresponding pathogen (fungi). However, the active ingredient mixture can also penetrate the plant through the roots via the soil (systemic action) by drenching the locus of the plant with a liquid formulation, or by applying the active ingredients in solid form to the soil, e.g. in granular form (soil application). In a particularly preferred method, the mixture of the active ingredients of formulae I and II may also be applied to plant propagation material, i.e. to seeds, tubers, fruit or other plant material to be protected (e.g. bulbs) (coating) by impregnating the seeds either with a liquid formulation of the fungicide or coating them with a solid formulation. In special cases other types of application are also possible, for example the specific treatment of plant cuttings or twigs serving propagation.

Suitable solvents are: aromatic hydrocarbons, the fractions containing 8 to 12 carbon atoms, typically xylene mixtures or substituted naphthalenes, phthalates such as dibutyl or dioctyl phthalate, aliphatic hydrocarbons such as cyclohexane or paraffins; alcohols and glycols and their ethers and esters such as monomethyl ether, ketones such as cyclohexanone, strongly polar solvents such as N-methyl-2-pyrrolidone, dimethyl sulfoxide or dimethyl formamide, as well as vegetable oils or epoxidised vegetable oils; or water.

The solid carriers typically used for dusts and dispersible powders are calcite, talcum, kaolin, montmorillonite or attapulgite, highly dispersed silicic acid or absorbent polymers. Suitable granulated adsorptive granular carriers are pumice, broken brick, sepiolite or bentonite, and suitable non-sorptive carriers are typically calcite or dolomite.

Depending on the nature of the active ingredients to be formulated, suitable surface-active compounds are nonionic, cationic and/or anionic surfactants having good emulsifying, dispersing and wetting properties. The term "surfactants" will also be understood as comprising mixtures of surfactants.

The surfactants customarily employed in formulation technology may be found in the following literature:

"Mc Cutcheon's Detergents and Emulsifiers Annual" MC Publishing Corp., Glen Rock, N.J., 1988.

M. and J. Ash, "Encyclopedia of Surfactants", Vol. I–III, Chemical Publishing Co., New York, 1980–1981.

The invention is illustrated by the following Examples wherein "active ingredient" signifies a mixture consisting of R-metalaxyl I and compound II in a specific mixing ratio.

| Wettable powders | a) | b) | c) |
| --- | --- | --- | --- |
| active ingredient [I:II = 6:1(a), 7:2(b), 2:3(c)] | 28% | 54% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenol polyethylene glycol ether (7–8 mol ethylene oxide) | — | 2% | — |
| highly dispersed silica | 5% | 10% | 10% |
| kaolin | 59% | 23% | — |

The active ingredient is thoroughly mixed with the adjuvants and the mixture is well ground in a suitable mill to give wettable powders which can be diluted with water to suspensions of any desired concentration.

| Emulsifiable concentrate | |
| --- | --- |
| active ingredient (I:II = 7:3) | 10% |
| octylphenol polyethylene glycol ether (4–5 mol ethylene oxide) | 3% |
| calcium dodecylbenzene sulfonate | 3% |
| castor oil polyglycol ether (35 mol ethylene oxide) | 4% |
| cyclohexanone | 30% |
| xylene mixture | 50% |

This concentrate is suitable for wet dressing plant propagation material. Emulsions of any desired concentration, which can be used for plant protection, can be prepared by diluting this concentrate with water.

| Extruder granulate | |
| --- | --- |
| active ingredient (I:II = 4:1) | 15% |
| sodium lignin sulfonate | 2% |
| carboxymethyl cellulose | 1% |
| kaolin | 82% |

The active ingredient is mixed with the adjuvants, the mixture is ground and moistened with water. This mixture is extruded and then dried in a stream of air.

| Coated granulate | |
| --- | --- |
| active ingredient (I:II = 5:3) | 8% |
| polyethylene glycol (MG 200) | 3% |
| kaolin | 89% |
| (MG = molecular weight) | |

The finely ground active ingredient is applied uniformly in a mixer to the kaolin which is moistened with polyethylene glycol to give non-dusting coated granulates.

| Suspensions concentrate | |
|---|---|
| active ingredient (I:II:III = 6:1:10) | 34% |
| propylene glycol | 10% |
| nonylphenol polyethylene glycol ether (15 mol Et-oxide) | 6% |
| sodium lignin sulfonate | 10% |
| carboxymethyl cellulose | 1% |
| silicone oil (in the form of a 75% aqueous emulsion) | 1% |
| water | 38% |

The finely ground active ingredient is intimately mixed with the adjuvants to give a suspension concentrate from which suspensions of any desired concentration can be prepared by dilution with water. Such dilutions can be used to treat living plants or seeds by spraying, pouring or immersing and to protect them from infestation by microorganisms.

BIOLOGICAL EXAMPLES

Fungicides have a synergistic effect whenever the fungicidal action of the active ingredient combination is greater than the sum of the actions of the active ingredients when applied individually.

The action E to be expected for a given active ingredient combination, for example of two fungicides, obeys the so-called COLBY formula and can be calculated as follows (COLBY, LR. "Calculating synergistic and antagonistic responses of herbicide combinations". Weeds 15, pages 20–22, 1967) (LIMPEL and al., 1062 "Weeds control by . . . certain combinations". Proc. NEWCL, Vol. 16, pp. 48–53):

(mg a.i./liter=milligrams of active ingredient per liter or a multiple thereof)

X=% action by fungicide I at p mg a.i./liter

Y=% action by fungicide II at q mg a.i./liter

E=the expected action of fungicides I+II at a rate of application of p+q mg a.i./liter (additive action), then according to Colby:

$$E = X + Y - \frac{X \cdot Y}{100}$$

If the action (O) actually observed is greater than the expected action, then the action of the combination is superadditive, i.e. there is a synergistic effect.

Such effects are observed in applications of mixtures of metalaxyl (having a high R-enantiomer content) and fludioxonil. Depending on the type of soil, the rate of degradation of such a mixture in the soil is two to four times as high as that of a mixture consisting of racemic metalaxyl and fludioxonil.

What is claimed is:

1. A fungicidal composition comprising synergistic fungicidally effective amounts of a mixture of metalaxyl, wherein more than 70% by weight of the metalaxyl is the R-enantiomer (I) and fludioxonil (II), and a fungicidally acceptable carrier.

2. The composition according to claim 1, wherein the ratio by weight of the mixture of I:II is from 10:1 to 1:30.

3. A composition according to claim 1, wherein the metalaxyl has an R-enantiomer content of more than 85% by weight.

4. A composition according to claim 3, wherein the metalaxyl has an R-enantiomer content of more than 92% by weight.

5. A composition according to claim 4, which comprises the use of pure R-metalaxyl which is substantially free of S-enantiomer.

6. A method of controlling or preventing fungal infestation in plants, parts of plants, seeds, or at their locus of growth, which comprises applying in any desired sequence, simultaneously or in succession, synergistic fungicidally effective amounts of a mixture of metalaxyl, having an R-enantiomer content of more than 70% by weight, and fludioxonil.

7. A method according to claim 6, wherein the R-enantiomer content of the metalaxyl used is more than 85% by weight.

8. A method according to claim 7, wherein the R-enantiomer content of the metalaxyl used is more than 92% by weight.

9. A method according to claim 8, wherein the metalaxyl component is pure R-metalaxyl which is substantially free of S-enantiomer.

10. A method according to claim 6, wherein Phytophthora spp, Plasmopara, Pythium, Pseudoperonospora, Bremia, Fusarium, Rhizoctonia and/or Botrytis are controlled.

11. A method according to claim 6, wherein the parts of plants are the propagation material.

12. A method according to claim 11, wherein the seeds are the propagation material.

* * * * *